US009895341B2

(12) United States Patent
Khoo et al.

(10) Patent No.: US 9,895,341 B2
(45) Date of Patent: Feb. 20, 2018

(54) INFLAMMATION AND IMMUNITY TREATMENTS

(75) Inventors: Christina Khoo, Lakeville-Middleboro, MA (US); DeAnn Liska, Battle Creek, MI (US); Susan S. Percival, Gainesville, FL (US)

(73) Assignees: Ocean Spray Cranberries, Inc., Lakeville-Middleboro, MA (US); University Of Florida Research Foundation, Incorporated, Gainesville, FL (US)

( * ) Notice: Subject to any disclaimer, the term of this patent is extended or adjusted under 35 U.S.C. 154(b) by 73 days.

(21) Appl. No.: 14/008,995

(22) PCT Filed: Mar. 30, 2012

(86) PCT No.: PCT/US2012/031581

§ 371 (c)(1),
(2), (4) Date: Feb. 3, 2014

(87) PCT Pub. No.: WO2012/135702

PCT Pub. Date: Oct. 4, 2012

(65) Prior Publication Data

US 2014/0134206 A1 May 15, 2014

Related U.S. Application Data

(60) Provisional application No. 61/471,073, filed on Apr. 1, 2011.

(51) Int. Cl.

| | |
|---|---|
| ***A61K 31/7048*** | (2006.01) |
| ***A61K 31/352*** | (2006.01) |
| ***A61K 45/06*** | (2006.01) |
| ***A61K 31/353*** | (2006.01) |
| ***A61K 39/00*** | (2006.01) |

(52) U.S. Cl.

CPC .......... *A61K 31/352* (2013.01); *A61K 31/353* (2013.01); *A61K 39/00* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 9,314,494 B2 * | 4/2016 | Hotchkiss .............. | A61K 36/45 |
| 9,371,313 B2 * | 6/2016 | Woolford ............. | A61K 31/352 |
| 2002/0054924 A1 | 5/2002 | Leahy et al. | |
| 2005/0019389 A1 | 1/2005 | Rozhon et al. | |
| 2009/0226548 A1 * | 9/2009 | Minatelli ............... | A61K 36/45 424/732 |

FOREIGN PATENT DOCUMENTS

| | | |
|---|---|---|
| EP | 1676572 | 7/2006 |
| JP | 2975997 | 11/1999 |
| JP | 2001-524938 | 12/2001 |
| JP | 2007-077122 | 3/2007 |
| JP | 2007-518812 | 7/2007 |
| JP | 2009-535417 | 10/2009 |
| JP | 2010-168300 | 8/2010 |
| WO | 1998/16111 | 4/1998 |
| WO | 2005/030200 | 7/2005 |
| WO | 2005/072762 | 8/2005 |
| WO | 2007/130882 | 11/2007 |
| WO | 2008/004224 | 1/2008 |
| WO | 2010/121203 | 10/2010 |

OTHER PUBLICATIONS

International Search Report and Written Opinion issued in PCT/US2012/31581 dated Jun. 28, 2012 (8 pages).

Notification Concerning Transmittal of International Preliminary Report on Patentability (Chapter I of the Patent Cooperation Treaty) issued in PCT/US2012/031581 dated Oct. 10, 2013 (6 pages).

Office Action issued in JP2014-502855 dated Dec. 17, 2015 (with English translation) (12 pages).

* cited by examiner

*Primary Examiner* — Agnieszka Boesen

(74) *Attorney, Agent, or Firm* — Fish & Richardson P.C.

(57) ABSTRACT

Therapeutic use of extracts containing proanthocyanidin including treating disorders, e.g., inflammatory disorders, e.g., inflammatory bowel disease, Crohn's disease, ulcerative colitis, indeterminate colitis, microscopic colitis, collagenous colitis, and irritable bowel syndrome. Methods of increasing a subject's immunological resistance to an infection and/or treating the infection. The infection can be, e.g., a bacterial, viral, or fungal infection. The methods can include, e.g., selecting a subject that has, or is at risk of developing, an infection, e.g., a bacterial, viral, or fungal infection, or a combination thereof; providing a composition comprising at least about 10% proanthocyanidin by weight; and administering to the subject an amount of the composition to the subject, to thereby increase a subject's immunological resistance to an infection and/or to treat the infection.

45 Claims, 8 Drawing Sheets

INFLAMMATION AND IMMUNITY TREATMENTS

CROSS-REFERENCE TO RELATED APPLICATIONS

This application is a 371 U.S. National of PCT/US2012/031581, filed Mar. 30, 2012, which claims the benefit of the filing date of U.S. Provisional Application No. 61/471,073, filed on Apr. 1, 2011, which are incorporated by reference in their entirety as part of this application.

TECHNICAL FIELD

This invention relates to treatment of inflammatory disorders associated with immune responses characterized by innate and adaptive immunity.

BACKGROUND

Inflammation is part of a complex biological response of vascular tissues to harmful stimuli, such as pathogens, damaged cells, and irritants. Inflammatory bowel disease (IBD) is a disorder of unknown etiology characterized typically by diarrhea, cramping, abdominal pains, weight loss, rectal bleeding, tiredness, anemia, fistulae, perforations, obstruction of the bowel, and/or frequent need for surgical intervention. It encompasses a number of disorders including Crohn's disease, ulcerative colitis, indeterminate colitis, microscopic colitis, and collagenous colitis. Such disorders may at times begin clinically with a more benign or milder presentation, resembling Irritable Bowel Syndrome (IBS), which can progress to increasing inflammation accompanying the IBS and may ultimately develop into full-blown IBD. The precise causes of IBD and IBS remain unknown. Considering the above described unwanted interactions and the undesired results, improved methods to treat IBD was desired to address these shortcomings.

SUMMARY

In one aspect, the present application provides methods of treating a subject, e.g., a subject having or at risk for an inflammatory disorder. The present specification provides methods of treating an inflammatory disorder in a subject, the methods comprising selecting a subject that has, or is at risk of developing, an inflammatory disorder; providing a composition comprising at least about 10% proanthocyanidin by weight; and administering a therapeutically effective amount of the composition to the subject, to thereby treat the inflammatory disorder in the subject.

In some embodiments, the inflammatory disorder can be, e.g., inflammatory bowel disease, Crohn's disease, ulcerative colitis, indeterminate colitis, microscopic colitis, collagenous colitis, and/or irritable bowel syndrome.

In some embodiments, the method further comprises administering a second treatment to the subject, e.g., administering an anti-inflammatory drug to the subject, e.g., a corticosteroid drug.

In another aspect, the present application provides methods of increasing a subject's immunological resistance to an infection and/or treating the infection. The infection can be, e.g., a bacterial, viral, or fungal infection. The methods can include, e.g., selecting a subject that has, or is at risk of developing, an infection, e.g., a bacterial, viral, or fungal infection, or a combination thereof, providing a composition comprising at least about 10% proanthocyanidin by weight; and administering to the subject an amount of the composition to the subject, to thereby increase a subject's immunological resistance to a infection and/or to treat the infection.

In still another aspect, the present application provides methods of modulating gastrointestinal tract flora levels in a subject. The method can include, e.g., administering to the subject an amount of a composition comprising at least about 10% proanthocyanidin by weight effective to increase the number of commensal bacteria in the gastrointestinal tract, decrease the number of pathogenic bacteria in the gastrointestinal tract, or increase the number of commensal bacteria and decrease the number of pathogenic bacteria in the gastrointestinal tract, thereby modulating gastrointestinal tract flora levels in the subject.

In some embodiments of the described methods, the composition comprises at least about 50% proanthocyanidin by weight. In some embodiments of the described methods, the composition comprises at least about 1% flavonol by weight. In some embodiments, the composition comprises about 70% proanthocyanidin by weight and about 10% flavonol by weight.

In some embodiments, an amount of the composition is administered to the subject such that the subject receives 20 to 500 mg of proanthocyanidin over 24 hours.

In some embodiments, the composition is administered orally, intravenously, and/or rectally.

In some embodiments, the methods described herein further include administering a known treatment for a disorder. For example, methods described herein can further include administering an antibiotic and/or an anti-inflammatory drug to the subject.

The treatments described herein can be administered to any subject, human or non-human. In some embodiments, the subject is a mammal, e.g., a human.

In one aspect, the present application provides compositions comprising at least about 10% proanthocyanidin by weight for use in the treatment of an inflammatory disorder in a subject.

In some embodiments, the inflammatory disorder is selected from the group consisting of inflammatory bowel disease, Crohn's disease, ulcerative colitis, indeterminate colitis, microscopic colitis, collagenous colitis, and irritable bowel syndrome.

In some embodiments, the composition is administered to the subject with an anti-inflammatory drug.

In another aspect, the present application provides compositions comprising at least about 10% proanthocyanidin by weight for use in increasing a subject's immunological resistance to a bacterial or viral infection.

In still another aspect, the present application provides compositions comprising at least about 10% proanthocyanidin by weight for use in modulating gastrointestinal tract flora levels in a subject, wherein administration of the composition to a subject increases the number of commensal bacteria in the gastrointestinal tract, decreases the number of pathogenic bacteria in the gastrointestinal tract, or increases the number of commensal bacteria and decreases the number of pathogenic bacteria in the gastrointestinal tract.

In some embodiments of the described compositions, the composition comprises at least about 50% proanthocyanidin by weight. In some embodiments, the composition comprises at least about 1% flavonol by weight. In some embodiments, the composition comprises about 70% proanthocyanidin by weight and about 10% flavonol by weight. In some embodiments, the composition is administered to a subject such that the subject receives 20 to 500 mg of proanthocyanidin over 24 hours. In some embodiments, the composition is administered orally, intravenously, or rectally. In some embodiments, the composition is administered to the subject with an antibiotic.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

The terms "effective amount" and "effective to treat," as used herein, refer to the administration of a pharmaceutical compositions(s) described herein in an amount or concentration and for period of time including acute or chronic administration and periodic or continuous administration that is effective within the context of its administration for causing an intended effect or physiological outcome. The terms "treat" or "treatment," are used herein to describe delaying the onset of, inhibiting, or alleviating the effects or symptoms of a disorder or condition, e.g., a disorder or condition described herein.

DETAILED DESCRIPTION

Figure 1A:
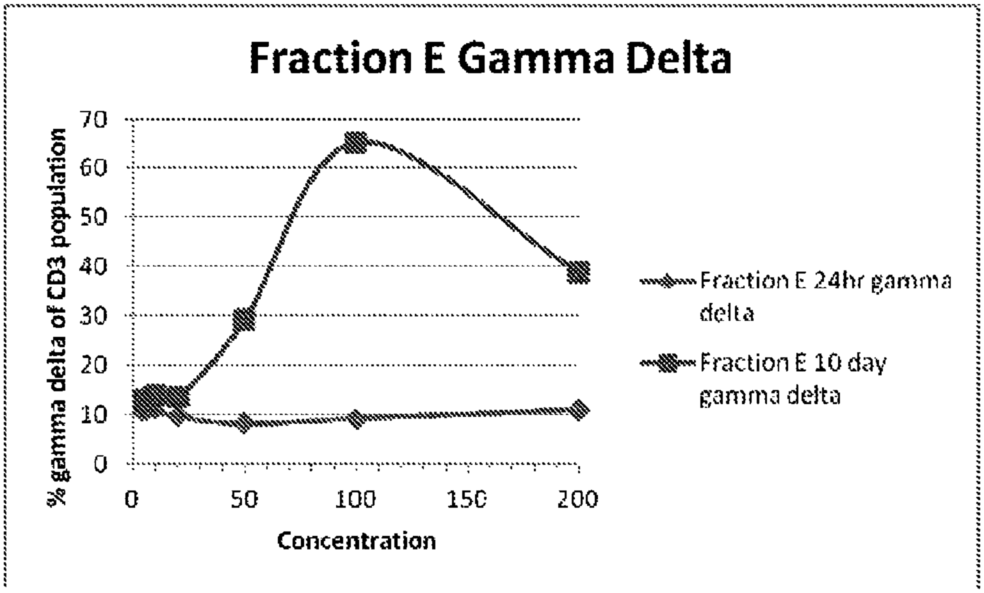
FIGS. 1A and 1B are line graphs showing the stimulatory effects of PAC enriched fractions E and F on gamma delta T cells.

The present application provides various methods of treatment using cranberry extracts, such as a proanthocyanidin containing extract. Exemplary extracts, and methods of making such extracts, are described herein and are also described, e.g., in Patent Cooperation Treaty (PCT) Application Serial Number PCT/US2010/031492, published as WO 2010/121203, which is incorporated herein in its entirety. The method can include, e.g., identifying a subject in need of treatment, and administering to the subject a pharmaceutically effective amount of an extract. For example, the method can involve identifying and treating a subject having or at risk for a disorder that involves inflammation (e.g., generalized or localized inflammation). For example, the method can involve treating a subject having or at risk for developing IBD (e.g., IBS, Crohn's disease, ulcerative colitis, indeterminate colitis, microscopic colitis, and/or collagenous colitis). As another example, the method can involve identifying and treating a subject that has or is at risk for developing an infection, e.g., a viral, bacterial, and/or fungal infection.

Extracts

Extracts (e.g., PACs-containing extracts and phenolics enriched extracts) obtained using the processes disclosed herein can be liquid, dry, semi dry, or powdered extracts (e.g., powdered, dehydrated, or lyophilized extracts) containing at least proanthocyanidins (PACs). Such extracts can be additionally characterized as having or containing a total amount of proanthocyanidins of at least about 1% (weight to volume (w/v), weight to weight (w/w), or volume to volume (v/v)), as assessed (e.g., quantified) using HPLC. For example, extracts can contain at least about or about 10%, e.g., at least about 20%, 30%, 40%, 50%, 60%, 70%, 80%, 90%, or at least about 95% (w/v, w/w, or v/v), or a range between any two of these values, proanthocyanidins, as assessed by HPLC. Such extracts can also contain at least about 1% (w/v, w/w, or v/v) flavonols, as assessed (e.g., quantified) using, e.g., HPLC. For example, extracts can contain at least about or about 2%, 3%, 4%, 5%, 6%, 7%, 8%, 9%, 10%, 11%, 12%, 15%, 20%, 25%, 30%, 35%, 40%, 50%, 60% (w/v, w/w, or v/v), more than 61%, 65%, 70%, 75%, or at least about 80% (w/v, w/w, or v/v), or a range between any two of these values, flavonols, as assessed by HPLC.

The levels of PACs in an extract can be assessed or quantified using DMAC (the DMAC method is disclosed in Cunningham et al., Analysis and Standardization of Cranberry Products, Quality Management of Nutraceuticals, ACS Symposium Series, 803ed., American Chemical Society, Washington D.C., pages 151-166, 2002, which is hereby incorporated by reference). In such instances, extracts containing at least proanthocyanidins can contain about or at least about 40% (w/v, w/w, or v/v) PACs, as assessed (e.g., quantified) using, e.g., DMAC. For example, extracts can contain at least about or about 40%, 50%, 55%, 60%, 70%, 80% (w/v, w/w, or v/v), more than 80% (w/v, w/w, or v/v), or a range between any two of these values PACs, as assessed by DMAC; and/or a ratio of flavonols to PACs of about 1:5 (e.g., about 1:2, 1:2.5, 1:3, 1:3.5, 1:4, 1.4.5, 1:5, 1:5.5, 1:6, 1.6.5, 1:7, 1:7.5, 1:8, 1:8.5, 1:9, 1:9.5, or about 1:10), wherein flavonols are assessed (e.g., quantified) using, e.g., HPLC, and PACS are assessed (e.g., quantified) using, e.g., HPLC or DMAC; and/or a PACs oligomeric profile that substantially the same or similar, (e.g., substantially similar) to the PACs oligomeric profile present in cranberry juice feedstock. Alternatively or in addition, the PACs oligomeric profile can include higher amounts of 2-mer and greater than 10-mers than other PACs oligomers. Alternatively or in addition, the PACs oligomeric profile can include ratios of PACs oligomers of about 6(1 mer):28(2 mer):11(3 mer):8(4 mer):6(5 mer):7(6 mer):3(7 mer):4(8 mer):2(9 mer):26(>10 mer); and/or a ratio of PACs to total phenolics that is substantially the same (e.g., roughly equal) to the ratio of PACs to total phenolics present in cranberries or the fruit from which the phenolics were extracted, e.g., present in cranberries or cranberry juice; and/or a ratio of PACs to quercetin, quercgalac, quercitrin, myricetin, and/or quercaraban that is the same (e.g., substantially the same) or similar, (e.g., substantially similar) to the ratio of PACs to quercetin, quercgalac, quercitrin, myricetin, and/or quercaraban present in cranberry juice; and/or a ratio of PACs to total anthocyanins that is not the same as the ratio of PACs to total anthocyanins in cranberries or the fruit from which the phenolics were extracted, e.g., present in cranberries or cranberry juice; and/or phenolics (e.g., polymeric phenolics) with a molecular weight (e.g., an average molecular weight) of less than 14,000 Daltons; and/or PACs (e.g., 10% or more of total PACs in the extract) with polymer chain lengths of 1, 2, 3, 4, 5, 6, 7, 8, 9, 10, or greater than 10, or combinations thereof; and/or a higher concentration of anthocyanin and PACs than is present in cranberries or the fruit from which the phenolics were extracted, e.g., present in cranberries or cranberry juice feedstock, e.g., a higher dry weight concentration.

Extracts containing at least PACs and flavonols can be optionally further characterized based on the levels of organic acids (e.g. total organic acids) and sugars (e.g., total sugars) in the extract. For example, extracts can contain less than 5% (w/v, w/w, or v/v) organic acids (e.g., about 5% or less than about 5%, 4%, 3%, 2%, 1% organic acids, less than 1% organic acids, no organic acids (e.g., the extract can be free (e.g., substantially free) of organic acids), or a range between any two of these values), and/or less than 5% sugar (e.g., about 5% or less than about 5%, 4%, 3%, 2%, 1% sugar, less than 1% sugar, no sugar (e.g., the extract can be free (e.g., substantially free) of sugar), or a range between any two of these values). In the event that another method is used for quantifying PACs for example the BL DMAC method as referenced Prior et al. (2010), an appropriate response factor is applied to the PAC value for equivalent comparisons.

The phenolics extracted using the process described herein can be soluble in aqueous media.

An extract can be formulated as a composition for use in an animal (e.g., a human and/or non-human animal), e.g., for ingestion or consumption by an animal (e.g., a human and/or non-human animal). Such compositions can include excipients, e.g., to increase the stability, solubility, shelf-life, taste, to standardize the level of a particular compound in the composition, and/or bioabsorption of the extract. Examples of includable excipients include but are not limited to, calcium carbonate, calcium phosphate, various sugars and types of starch, cellulose derivatives, gelatin, vegetable oils, polyethylene glycols, propylene glycol, and inhibitors of enzymes that degrade and/or modify phenolics, such as inhibitors of polyphenoloxidases, peroxidases, glycosidases, decarboxylases, and esterases. Alternatively or in addition, the extracts can be combined with agents that protect them from oxidative reactions (e.g., anti-oxidants). Different diafiltration media (e.g., acidified water) can be employed to stabilize and/or adjust the color of the extract.

PAC-containing solutions can be administered as a single bolus or as an infusion over one or more hours or days. Further, PAC-containing solutions can be administered at the same time and length as antibiotic treatment or every day for subjects, e.g., those who have, are suspected of having, or are at risk for developing an inflammatory disorder. Optimal dosage levels can be readily determined by a skilled practitioner, such as a physician, e.g., a gastroenterologist. Exemplary dosages of PACs include, e.g., about 40 mg a day, about 50 mg a day, about 80 mg a day, about 100 mg a day, about 120 mg a day, about 150 mg a day, about 160 mg a day, about 200 mg a day, about 240 mg a day, about 250 mg a day, about 280 mg a day, about 300 mg a day, about 320 mg a day, about 400 mg a day, about 500 mg a day, about 600 mg a day, and about 1000 mg a day, and dosages that fall within a range between any two of these values.

In some embodiments, any of the methods described herein can include an initial step of identifying a subject as one who has, is suspected of having, or at risk of having an inflammatory disorder.

Inflammatory Disorders

The methods of the present invention can be used to treat inflammatory disorders. The terms "inflammatory disorder(s)" and "inflammation" are used to describe the fundamental pathological process consisting of a dynamic complex of reactions (which can be recognized based on cytologic and histologic studies) that occur in the affected blood vessels and adjacent tissues in response to an injury or abnormal stimulation caused by a physical, chemical or biologic agent, including the local reactions and resulting morphologic changes, the destruction or removal of the injurious material, and the responses that lead to repair and healing. Inflammation is characterized in some instances by the infiltration of immune cells such as monocytes/macrophages, natural killer cells, and/or lymphocytes (e.g., B and T lymphocytes) into the area of tissue. In addition, inflamed tissue may contain cytokines and chemokines that are produced by the cells that have infiltrated into the area. Inflammation can be accompanied by thrombosis, including both coagulation and platelet aggregation. The term inflammation includes various types of inflammation such as acute, chronic, allergic (including conditions involving mast cells), alterative (degenerative), atrophic, catarrhal (most frequently in the respiratory tract), croupous, fibrinopurulent, fibrinous, immune, hyperplastic or proliferative, subacute, serous and serofibrinous. Inflammation localized in the gastrointestinal tract, or any portion thereof, kidneys, liver, heart, skin, spleen, brain, kidney, pulmonary tract, and the lungs may favorably be treated using the methods of the present invention. Generalized inflammation associated with shock, e.g., septic shock, hemorrhagic shock caused by any type of trauma, and anaphylactic shock, may favorably be treated using the methods of the present invention. Further, it is contemplated that the methods of the present invention can be used to treat rheumatoid arthritis, lupus, and other inflammatory and/or autoimmune diseases, heightened inflammatory states due to immunodeficiency, e.g., due to infection with HIV, and hypersensitivities.

Inflammatory Bowel Disease

The methods of the present invention may be used to treat IBD in a subject. IBD is a group of inflammatory conditions of the colon and small intestine. The major types of IBD are Crohn's Disease and ulcerative colitis (UC). The main difference between Crohn's Disease and UC is the location and nature of the inflammatory changes. Crohn's Disease can affect any part of the gastrointestinal tract, from mouth to anus (skip lesions), although a majority of the cases start in the terminal ileum. UC, in contrast, is restricted to the colon and the rectum. Although very different diseases, both may present with any of the following symptoms: abdominal pain, vomiting, diarrhea, rectal bleeding, severe internal cramps/muscle spasms in the region of the pelvis, weight loss and various associated complaints or diseases like arthritis, pyoderma gangrenosum, and primary sclerosing cholangitis. Diagnosis is generally by colonoscopy with biopsy of pathological lesions. IBD is often treated with anti-inflammatory drugs, e.g., mesalazine, though it is more useful in UC than in Crohn's disease. Generally, depending on the level of severity, IBD may require immunosuppression, such as prednisone, TNF inhibition, azathioprine, methotrexate, or 6-mercaptopurine, to control symptoms. Often, steroids are used to control disease flares and were once acceptable as a maintenance drug. Severe cases may require surgery, such as bowel resection, strictureplasty, or a temporary or permanent colostomy or ileostomy. Treatments described herein may be combined with any one or more of such known treatments.

Ulcerative Colitis

The methods of the present invention may also be used to treat UC in a subject. UC is a type of IBD that affects the lining of the large intestine (colon) and rectum. The cause of UC is unknown. People with this condition have problems with the immune system, but it is not clear whether immune problems cause this illness. Although stress and certain foods can trigger symptoms, they do not cause UC. UC may affect any age group, although there are peaks at ages 15-30 and then again at ages 50-70. The disease usually begins in the rectal area, and may involve the entire large intestine over time. Risk factors include a family history of UC, or Jewish ancestry. The symptoms vary in severity and may start slowly or suddenly. About half of people only have mild symptoms. Others have more severe attacks that occur more often. Many factors can lead to attacks, including respiratory infections or physical stress. Symptoms include: abdominal pain and cramping that usually disappears after a bowel movement, abdominal sounds (a gurgling or splashing sound heard over the intestine), blood and pus in the stools, diarrhea (from only a few episodes to very often throughout the day), fever, tenesmus (rectal pain), and weight loss.

Gastrointestinal Tract Flora

The gastrointestinal tract flora consists of microorganisms that normally live in the digestive tract of animals. Research suggests that the relationship between gut flora and humans is not merely commensal, but rather a mutualistic, symbiotic relationship (Sears, *Anaerobe,* 11: 247, 2005). The microorganisms perform a host of useful functions, including preventing growth of harmful species (Guarner and Malagelada, *Lancet,* 361:512, 2003), fermenting unused energy substrates, training the immune system, regulating the development of the gut, producing vitamins for the host (such as biotin and vitamin K), and producing hormones to direct the host to store fats. However, in certain conditions, some bacterial species are thought to be capable of causing disease.

Provided herein are methods for modulating gastrointestinal tract flora levels in a subject. The present invention relates to methods of treating subjects with reduced levels and/or function of gastrointestinal tract flora by administering a PACs-containing extract in an amount effective to increase or preserve the number of commensal bacteria and composition of intestinal microbiota. This invention also relates to methods of treating subjects with a PACs-containing extract to treat infections by pathogenic bacteria and/or inhibit the growth or decrease the number of pathogenic bacteria in the gastrointestinal tract. The methods described can be used to treat symptoms associated with reduced levels of commensal bacteria and/or function of gastrointestinal tract flora, e.g., antibiotic-associated diarrhea (AAD), *Clostridium difficile*-associated disease (CDAD), acquired immunodeficiency syndrome (AIDS), hypothyroidism, colorectal carcinoma, obesity, rheumatoid arthritis, eczema, allergy, radiotherapy, chemotherapy, stress, and food poisoning.

Approximately $10^{14}$ bacteria can be found in a normal human gastrointestinal tract (Kullberg, *Nature,* 453:602, 2008; Baba et al., *J Leukoc Biol,* 84:468, 2008). Levels of gastrointestinal tract flora can be determined by measuring the number of bacteria in a stool sample. Normal levels of bacteria found in stool samples range from $10^9$ to $10^{13}$ CFU/gram of dry stool (Chen et al, *J Dairy Sci,* 82:2308, 1999). Alternatively, normal levels of bacteria found in stool samples can be determined by examining the stool samples from at least 20 subjects who do not have gastrointestinal problems associated with altered levels of flora (e.g., caused by AAD, CDAD, AIDS, hypothyroidism, food poisoning, obesity, IBD, IBS, colorectal carcinoma, obesity, rheumatoid arthritis, eczema, allergy, undergoing radiotherapy or chemotherapy treatment, or under stress).

General Methodology

The methods can be used as a treatment for inflammatory bowel disease, e.g., Crohn's disease, UC, microscopic colitis, collagenous colitis, irritable bowel syndrome, or any diagnosed reduction in the level and/or function of normal gut flora, such as for diagnosed AAD, or can be used prophylactically, e.g., with any administration of an antibiotic in all subjects or in certain subject populations, e.g., those subjects over 60 years of age and subjects who have a compromised immune system (e.g., acquired immunodeficiency syndrome (AIDS) subjects and others). Other populations at higher risk are subjects who have had abdominal surgery, are prescribed a prolonged use of antibiotics, or who have been in the hospital for more than 2, 3, or 4 weeks. The methods are simple and effective and involve administering an effective amount of a PACs-containing extract.

Subjects to be Treated in Accordance with the Methods

In some embodiments, the subject is suspected of having, is at risk of having, or has an autoimmune disease, which can be, for example, multiple sclerosis (MS), rheumatoid arthritis (RA), insulin-dependent diabetes mellitus (IDDM), Crohn's disease, psoriasis, Behçet's disease, ankylosing spondylitis, systemic lupus erythematosus, or muscular dystrophy. A subject "suspected of having an autoimmune disease" is one having one or more symptoms of the condition. Symptoms of the condition vary greatly and are well-known in the art. They include, for example, elevated fever, hair loss, hyperpigmentation, skin rash, skin ulcers, dry eyes, blurred vision, dry mouth, chronic fatigue, insomnia, muscle weakness, joint stiffness, nausea, vomiting, shortness of breath, and hypoglycemia. A subject "at risk of having an autoimmune disease" is one who has (i) a family history of (a genetic predisposition for) such disorders or (ii) one or more risk factors for having an autoimmune disease. Risk factors include, for example, exposure to factors that trigger pathological inappropriate immune responses to self-components. Such factors include, for example, infectious agents (e.g., viral, bacterial, or fungal, including yeast, microorganisms) or antigenic substances produced by them. From the above it will be clear that neither subjects "suspected of having an autoimmune disease" nor subjects "at risk of having an autoimmune disease" are all the subjects within a species of interest.

In one aspect of the methods described herein, the subject has, or is at risk of developing, cancer, or a viral, bacterial, or fungal infection. In some embodiments of the methods described herein, the subject has, or is at risk of developing, cancer, e.g., leukemia, lymphoma, multiple myeloma, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer. A subject that "has, or is at risk of developing, cancer" is one having one or more symptoms of and/or known risk factors for, cancer, as identified by a health care provider. Symptoms of cancer vary greatly and are well-known to those of skill in the art and include, without limitation, breast lumps, nipple changes, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, or pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, pancreas metastases, difficulty swallowing, and the like. A subject that is "at risk of developing cancer" is one that has a predisposition to develop cancer (i.e., a genetic predisposition develop cancer such as a mutation in a tumor suppressor gene, e.g., BRCA1, p53, RB, or APC) or has been exposed to conditions that can result in cancer. Thus, a subject that is "at risk of developing cancer" can be one that has been exposed to mutagenic or carcinogenic levels of certain compounds (e.g., carcinogenic compounds in cigarette smoke such as acrolein, arsenic, benzene, benz{a}anthracene, benzo{a}pyrene, polonium-210 (Radon), urethane, or vinyl chloride). Moreover, the subject can be "at risk of developing cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T cell leukemia-lymphoma virus. A health care provider can identify a subject who is at risk of developing cancer based on the above factors and/or the general knowledge in the art.

In some embodiments of the methods described herein, the subject has, or is at risk of developing, a viral infection, e.g., influenza virus, rhinovirus, varicella zoster virus, human immunodeficiency virus, human papillomavirus, herpes simplex virus, hepatitis A/B/C/D/E/F/G virus, hemorrhagic fever virus, Coronavirus, SARS virus, smallpox virus, vaccinia virus, variola virus, West Nile virus, Ebola virus, cowpox virus, monkeypox virus, or simian immunodeficiency virus. A subject that "has, or is at risk of developing, a viral infection" is one having one or more symptoms of the condition. Symptoms of a viral infection vary greatly and are known to those of skill in the art and include, without limitation, malaise, fever, chills, decreased appetite, dehydration, headaches, tachypnoea, hypoxemia, and diaphoresis. Common viral infections may be diagnosed based on symptoms. Blood may be tested for antibodies to viruses or for antigens. Polymerase chain reaction (PCR) techniques may be used to make many copies of the viral genetic material, enabling doctors to rapidly and accurately identify the virus. A subject that is "at risk of developing a viral infection" is one that has been exposed to conditions that can result in a viral infection or is immunocompromised. An immunocompromised subject may be particularly vulnerable to opportunistic infections, in addition to infections that affect subjects with normal immune systems.

In one aspect of the methods described herein, the subject has, or is at risk of developing, a bacterial infection, e.g., *Bacillus anthracis, Bacillus subtilis, Bordetella pertussis, Campylobacter jejuni, Campylobacter pylori, Chlamydia trachomatis, Clostridium botulinum, Clostridium difficile, Clostridium perfringens, Clostridium tetani, Corynebacterium diphtheriae, Corynebacterium fusiforme, Enterococcus faecalis*, enteropathogenic *Escherichia coli, Haemophilus influenzae, Helicobacter pylori, Klebsiella pneumoniae, Listeria monocytogenes, Mycobacterium tuberculosis, Neisseria gonorrhoeae, Pseudomonas aeruginosa, Rickettsia rickettsii, Salmonella typhimurium, Shigella dysenteriae, Staphylococcus aureus, Streptococcus faecalis, Streptococcus pneumoniae, Streptococcus pyogenes, Vibrio cholerae*, or *Yersinia pestis*. A subject that "has, or is at risk of developing, a bacterial infection" is one having one or more symptoms of the condition. Symptoms of a bacterial infection vary greatly and are known to those of skill in the art and include, without limitation, malaise, fever, chills, decreased appetite, dehydration, headaches, tachypnoea, hypoxemia, and diaphoresis. A bacterial infection can be diagnosed by culturing a sample (e.g., blood or urine) to determine the bacterial species present in the sample. A subject that is "at risk of developing a bacterial infection" is one that has an open wound or is immunocompromised. An immunocompromised subject may be particularly vulnerable to opportunistic infections, in addition to infections that affect subjects with normal immune systems.

In some embodiments of the methods described herein, the subject has, or is at risk of developing, a fungal infection, e.g., *Candida albicans, Candida glabrata, Candida parapsilosis, Candida utilis, Aspergillus fumigatus, Aspergillus flavus, Cryptococcus neoformans, Histoplasma capsulatum, Pneumocystis jirovecii*, or *Stachybotrys chartarum*. A subject that "has, or is at risk of developing, a fungal infection" is one having one or more symptoms of the condition. Symptoms of a fungal infection vary greatly and are known to those of skill in the art and include, without limitation, fever, cough, chest pain, severe headaches, and breathlessness. A fungal infection can be diagnosed by culturing a sample (e.g., blood or urine) to determine the fungal species present in the sample. A subject that is "at risk of developing a fungal infection" is one that has an open wound or is immunocompromised. An immunocompromised subject may be particularly vulnerable to opportunistic infections, in addition to infections that affect subjects with normal immune systems.

After profiling and characterizing a subject, a medical practitioner (e.g., a physician) can select an appropriate therapeutic modality for the subject (e.g., PACs-containing extract). Selecting a therapy for a subject can be, e.g.: (i) writing a prescription for a medicament; (ii) giving (but not necessarily administering) a medicament to a subject (e.g., handing a sample of a prescription medication to a subject while the subject is at the physician's office); (iii) communication (verbal, written (other than a prescription), or electronic (email, post to a secure site)) to the subject of the suggested or recommended therapeutic modality (e.g., PACs-containing extract); or (iv) identifying a suitable therapeutic modality for a subject and disseminating the information to other medical personnel, e.g., by way of subject record. The latter (iv) can be useful in a case where, e.g., more than one therapeutic agent are to be administered to a subject by different medical practitioners.

The methods are effective for a variety of subjects including mammals, e.g., humans and other animals. Veterinary applications are contemplated, such as laboratory animals, e.g., mice, rats, rabbits, or monkeys, or domesticated and farm animals, e.g., cats, dogs, goats, sheep, pigs, cows, or horses.

Methods of Administration

In general, PACs-containing extract can be administered orally, intravenously, or rectally with or without standard pharmaceutically acceptable excipients. These dosages can be administered as a single bolus or as an infusion over one or more hours or days. Further, PACs-containing extract can be administered at the same time and length as a separate treatment for the inflammatory disorder or every day for subjects who have, or at risk of developing, acquired immunodeficiency syndrome (AIDS), hypothyroidism, colorectal carcinoma, obesity, rheumatoid arthritis, eczema, allergy, stress, food poisoning, or undergoing radiotherapy or chemotherapy treatment.

As far as efficacy is concerned, oral administration may be suitable. For instance, PACs-containing extract can be administered in beverages (e.g., water, milk, juice, soda, and other flavored liquids), yogurt (e.g., plain or flavored yogurt, yogurt drinks, and frozen yogurt), and foods (e.g., cereal, cereal bars, energy bars, and ice cream). The liquid or powder form of PACs-containing extract can be taken by adding an additive such as a sweetener if necessary. A variety of well-known substances such as bonding agents, forming agents, lubricants, brightening agents, sweeteners, and zests, can be used. One is not restricted by these additional methods. Additionally, various methods can be used when combining PACs-containing extract with conventional beverages and foods. In such cases, the amount of PACs-containing extract used can be appropriately adjusted according to an individual's eating and drinking habits.

Dosage Forms

The compositions may be available in the form of a tablet containing PACs-containing extract in a powdered form. Alternatively, compositions may be in the form of a tablet capsule containing PACs-containing extract in a microencapsulated form. As a further possibility, present compositions may be in the form of a tablet capsule containing PACs-containing extract in a microgranulated form. In additional possibilities, the present compositions may be in the form of a tablet containing PACs-containing extract within a capsule, a capsule containing PACs-containing extract within a tablet, or any combination of the above.

The present methods may be carried out by administration of one or more tablets/capsules containing PACs-containing extract as described above. The present compositions may be prepared by means known in the art for the preparation of pharmaceutical compositions including blending, grinding, homogenizing, suspending, dissolving, emulsifying, dispersing, and, where appropriate, mixing of cranberries together with selected excipients, diluents, carriers, and adjuvants.

For oral administration, the present compositions may be in the form of tablets, lozenges, pills, troches, capsules, elixirs, powders, including lyophilized powders, solutions, granules, suspensions, emulsions, syrups, and tinctures. Slow-release, or delayed-release, forms may also be prepared, for example in the form of coated particles, multilayer tablets, or microgranules.

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose, or polyethylene glycol (PEG). Suitable sweeteners include sucrose, lactose, glucose, aspartame, saccharine, or natural sweeteners derived from plants such as Reb A and the like. Suitable disintegrating agents include corn starch, methylcellulose, polyvinylpyrrolidone, xanthan gum, bentonite, alginic acid, or agar. Suitable diluents include lactose, sorbitol, mannitol, dextrose, kaolin, cellulose, calcium carbonate, calcium silicate, or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac, or gluten. Suitable preservatives include sodium benzoate, vitamin E, alpha-tocopherol, ascorbic acid, methyl paraben, propyl paraben, or sodium bisulphite. Suitable lubricants include magnesium stearate, stearic acid, sodium oleate, sodium chloride, or talc. Suitable time delay agents include glyceryl monostearate or glyceryl distearate.

Liquid forms for oral administration may contain, in addition to the above agents, a liquid carrier. Suitable liquid carriers include water, oils, such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinyl-pyrrolidone, sodium alginate, or ceryl alcohol. Suitable dispersing agents include lecithin, polyoxyethylene esters of fatty acids such as stearic acid, polyoxyethylene sorbitol mono- or di-oleate, -stearate or laurate, polyoxyethylene sorbitan mono- or -dioleate, -stearate or -laurate, and the like.

Emulsions for oral administration may further include one or more emulsifying agents. Suitable emulsifying agents include dispersing agents as exemplified above or natural gums such as gum acacia or gum tragacanth.

Variations, modifications, and other implementations of what is described herein will occur to those of ordinary skill without departing from the spirit and the scope of the present disclosure. Accordingly, these are not to be limited only to the preceding illustrative description.

For additional illustrative features that may be used with the present compositions and methods, including the embodiments described here, refer to the documents listed herein, which are incorporated by reference in their entirety. All operative combinations between the above described illustrative embodiments and those features described in documents and references cited herein are considered to be potentially patentable embodiments.

EXAMPLES

The invention is further described in the following examples, which do not limit the scope of the invention described in the claims.

Example 1: Fractionation of Cranberry

Preparation of an Aqueous Cranberry Solution Using C18 Flash Chromatography

Cranberry concentrate powder (60 g) was added to a 2 L beaker with 1 L distilled water. The mixture was loaded onto a C18 Flash Chromatography column and washed sequentially with 500 ml distilled water and 500 ml 15% methanol:

distilled water. The eluent was discarded. The column was eluted with 500 ml 1% acetic acid in methanol and the eluent was collected.

LH20 Gel Chromatography

Column was pre-flushed with 500 ml distilled water. The methanol effluent from the C18 column was loaded on LH20 column (~150 ml). Column was washed with 500 ml distilled water. Then 500 ml 50% ethanol:distilled water was used to elute Fractions B and C. Fractions B and C were further separated by an ethyl acetate liquid separation in a separation funnel. Fraction B was isolated in the aqueous phase and Fraction C was in the solvent phase. The LH20 column was further eluted with 500 ml 70% acetone: distilled water and the eluent collected to obtain Fraction A. Fraction F was similarly obtained as Fraction A. The solvent can be evaporated off under vacuum (Bucchi—P3) and the liquid frozen at −80° C. (~150 ml).

In an exemplary method, Fraction E can be obtained as described in WO 2010/121203, hereby incorporated by reference in its entirety.

TABLE 1

Properties of PACs-Containing Extracts, Fractions A, B, C, E, and F

| | Fraction | | | | |
|---|---|---|---|---|---|
| | A | B | C | E | F |
| total weight (mg) | 1000 | 86 | 115 | 5000 | 1000 |
| PACS % | 80-95 | | 40-55 | 55-85 | 80-95 |
| Organic acids % | | | | 1 | |
| Carbohydrate % | | 67.5 | | 1 | |
| Phenolic acids % | 6.4 | 21.06 | 1 | 6 | 2.7 |
| Anthocyanins % | 1 | 10.8 | 14 | 13 | 15.5 |
| Flavonols % | 2 | 0.27 | 34 | 10 | |
| Total | 99.4 | 99.63 | 100 | 101 | 100.2 |

Example 2: Cranberry PACs Reduces Pathogenic Bacteria

Cranberry powder and fractions were incubated with fecal bacteria using an in vitro batch assays with complex "mixed" cultures to reflect endogenous flora. Bacteria cultures were evaluated by plate counts after incubation for 8 hours with cranberry materials. Materials were assessed and results are shown in Table 2 below. The results show that cranberries can support gut health by reducing putative pathogenic bacteria without affecting beneficial bacteria. A PAC enriched fraction can be utilized for more selective effects on gut flora.

TABLE 2

Effect of Cranberry Powder and Fraction F to Reduce Numbers of Bacteria

| | Total anaerobes | *Clostridia* | *Enterococcus* | *Lactobacillus* |
|---|---|---|---|---|
| Cranberry concentrate from whole fruit | Decreased | Decreased | Decreased | No change |
| PAC enriched (F) | | | Decreased | No change |

Example 3: PACs-Containing Extracts Increase Gamma Delta T Cells Proliferation

Blood was collected from fasting subjects into citrate dextrose tubes for PBMC acquisition, and one 10 mL SST™ tube (Vacutainer, Becton Dickinson, Franklin Lakes, N.J.) for serum under sterile conditions. Serum was removed after centrifugation (2000×g, 10 min, 4° C.) and used as autologous serum in assays set up on the day of each blood draw.

To obtain PBMC, whole blood was diluted 1:1 saline, and centrifuged at 800 g for 20 minutes at 20° C. layered over Lympholyte H® Cell Separation Media (Cedarlane Laboratories Ltd., Hornby, Ontario. The mononuclear cell layer was removed and washed twice with RPMI-1640 (Cellgro; Mediatech, Herndon, Va.) complete. Cell pellets were resuspended in 2 mL RPMI-1640 complete, and counted on a hemocytometer.

On the day of blood collection, $0.5\times10^6$ PBMCs were stained with cell surface markers to determine the percentage of specific cell populations in the PBMC suspension and $1.0\times10^6$ PBMCs in 1 mL RPMI-1640 complete medium containing 10% autologous serum and 32.5 U/mL of recombinant human IL-2 (BD Biosciences, San Diego, Calif.), were placed in duplicate wells of a 24-well tissue culture plate (Costar, Corning, N.Y.). The PACs-containing extracts were used at various concentrations to activate or cause proliferation of the cells. Plates were incubated in a humidified, 5% $CO_2$ atmosphere at 37° C. for 24 or 48 hours or 5 days. Ultimately, the concentrations that were most useful did not result in significant cell death and the cells were stimulated to proliferate or express surface markers.

Cultured cells were harvested and stained for 30 minutes, fixed with 1% paraformaldehyde, and read on a three color fluorescence FACsort Flow Cytometer (Becton Dickinson). Data was collected as a percentage of cells from quadrant dot blots while markers of activation were determined from the intensity of fluorescence in the gated population. The extract labeled Fraction A stimulated the proliferation of gamma delta T cells while Fractions B and C did not appear to have the same effect.

TABLE 3

Percent of Gamma Delta Cell Proliferation and Activation in Five Days

| Treatment | % of Gamma Delta T Cells Proliferation | Gamma Delta T cells Activation (fluorescent intensity) |
|---|---|---|
| Positive control | 5 | 1000 |
| Negative control | 2.5 | 200 |
| Fraction A (100 μg) | 9 | 3400 |
| Fraction B (100 μg) | 3 | 600 |
| Fraction C (100 μg) | 3 | 200 |

Figure 1B:
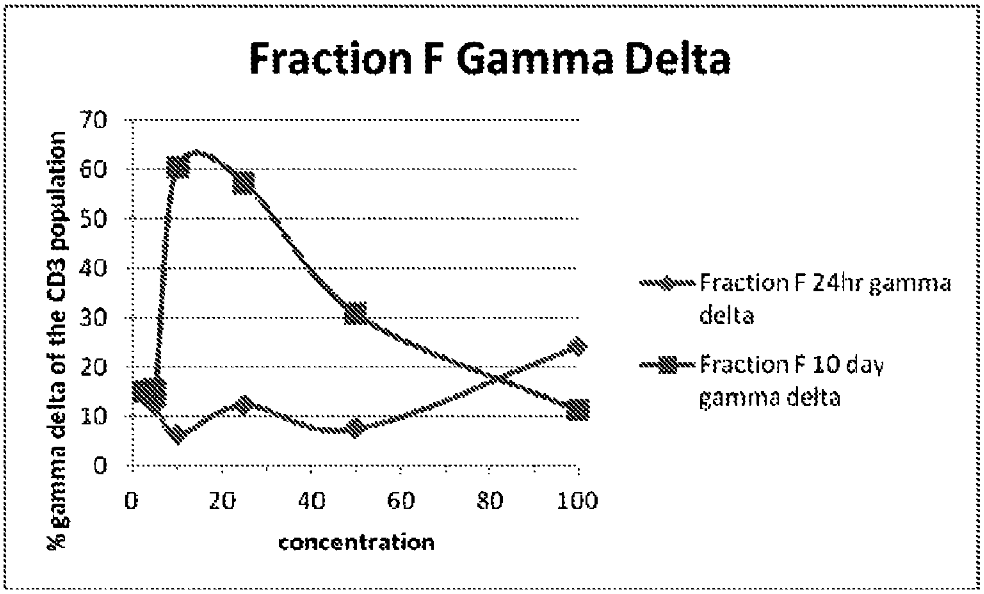

The composition of the extracts suggests that both PACS and flavonols are important for the activity but the presence of other components do not undermine the activity of the active compounds. A separate study tested Fractions E and F using the same protocol. Fraction E stimulated gamma delta T cells after 10 day incubation. The results showed that PAC enriched fractions E and F stimulated gamma delta T cells. (FIGS. 1A and 1B).

Figure 2:
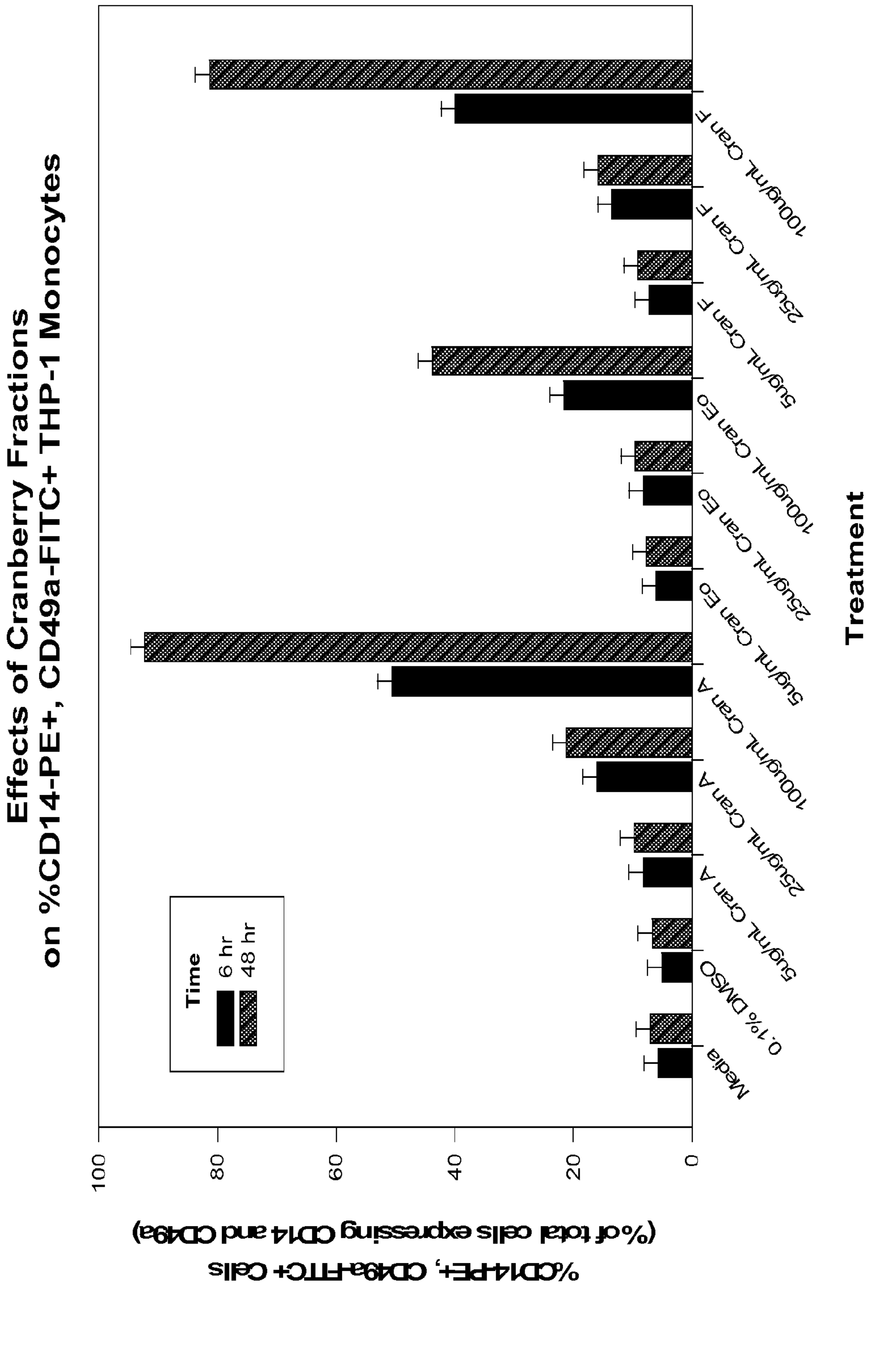
FIG. 2 is a bar graph showing the stimulatory effects of cranberry Fractions A, E, and F on expression of CD14 and CD49a in THP-1 monocytes.
Figure 3:
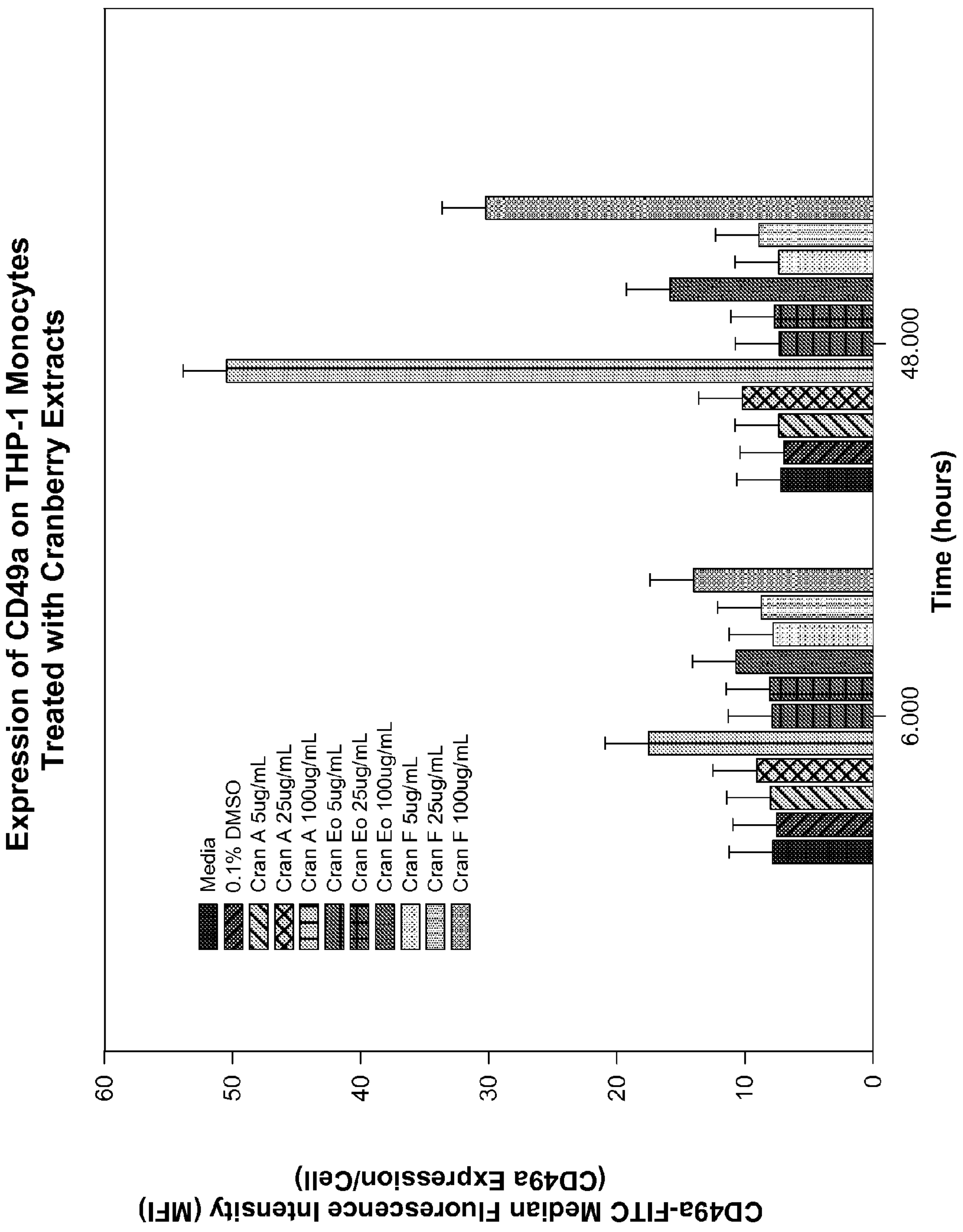
FIG. 3 is a bar graph depicting the induced expression of CD49a in THP-1 monocytes by cranberry Fractions A, E, and F.

Example 4: Effect of PACs-Containing Extracts A, E, and F on CD14 and CD49 Expression of THP-1 Monocytes 0.5 mL of THP-1 monocytes at $1\times10^6$ cells/mL were plated in 24 well plates. Serial dilutions of PACs-containing extracts A, E, and F were then made by dissolving each extract in DMSO to yield final concentrations of 5 mg/mL, 25 mg/mL, and 100 mg/mL. Each treatment and control was then further diluted into RPMI 1640 media at 1 μL treatment or control to 0.5 mL media. 0.5 mL of treatment/media or control/media dilutions was added to respective wells of the 24-well plate in duplicate. The final concentration of treatments in respective wells was 5 μg/mL, 25 μg/mL, and 100 μg/mL for each cranberry fraction. The final percentage of DMSO in DMSO control wells and cranberry fraction wells was 0.1%. Treated cells were incubated for time periods of 6 hours and 48 hours. At each time point, cells were harvested, stained with CD14-PE and CD49a-FITC antibodies, and fixed for flow cytometry analysis. Fractions A, E, and F were able to stimulate CD14 and CD49a expression suggesting activation of THP-1 monocytes (FIGS. 2 and 3).

Example 5: PACs-Containing Extracts Decrease Inflammatory Genes and Improve Immune Function The human monocytic cell line was treated with two PACs-containing extracts, Fraction E and cranberry concentrate powder (100 mg/mL), and subsequently challenged with lipopolysaccharides (LPS, 100 ng/mL). Three different doses (25, 50, and 100 mg/mL) were tested. The GENECHIP® Human Genome U133A 2.0 Array is a single array representing 14,500 well-characterized human genes. The results suggest that a list of 556 genes ($p<0.05$) that were significantly affected by treatments. Gene expression microarrays identified several immune related genes that were responsive to PACs-containing extracts (Fraction E and cranberry concentrate powder). A subset of genes was examined in more detail. Fraction E significantly increased MSR1 (macrophage scavenger receptor) and MTF1 (metallothionein 1F). These proteins are involved in host responses to protect against oxidative stress. The activity is more pronounced on the extract than the whole cranberry powder.

The most sensitive genes to Fraction E were CSF2, OAS1, MT1F and CCNL2. Whole concentrate powder have significantly lower effects. These genes are modified by cytokines and other inflammatory markers and show that cranberries and its components possess therapeutic effects on inflammation and immune functions. These findings suggest that supplementation with cranberry polyphenols may modulate the inflammation and immune processes.

TABLE 4

Microarray and RT-PCR Analysis Confirms Changes in Response to Extract and Concentrated Powder

| Gene Immune Response | Extract E | Concentrated Powder |
|---|---|---|
| MSR1 | up | No change |
| MT1F | up | No change |
| CSF2 | down | Down |
| HerC5 | down | No change |
| IFIT3 | down | No change |
| OAS1 | down | No change |
| IFIT1 | down | No change |
| CCLN2 | down | Down |

Example 6: Effect of Cranberry Phenolics on LPS Induced Nitric Oxide Synthase

Macrophage Cell Culture:

RAW 264.7 murine macrophages were grown on 24 well culture plates using DMEM (with phenol red), 10% FBS, 1% penicillin/streptomycin, and 1% L-alanyl-L-glutamine. When cells reached confluence, the cranberry phenolics from the cranberry powder (purified by pre-conditioned reverse phase column (C18, Waters Sep-Pak), rinsing with water, and then eluting with methanol) were added to DMEM media (without phenol red, 0.5% FBS, 1% penicillin/streptomycin and 1% L-alanyl-L-glutamine) at 25, 50, 100, and 200 μg gallic acid equivalents of cranberry polyphenols (GAE)/ml media (n=4). The media was replaced with media containing no lipopolysaccharide (LPS), 100 ng LPS/ml media (*E. coli* 055:B5, Sigma L6529), or 100 ng LPS/ml media with 0-200 μg GAE/ml media (as described above) and incubated for 4 hours. The media was removed, cells were washed with phosphate buffered saline (PBS) and lysis buffer with protease inhibitors was added to dissolve the cells. After homogenization, 50 μg of protein as analyzed per sample was loaded onto a 7.5% acrylamide SDS-PAGE gel with 5% acrylamide stacking gel. After separation, the proteins were transferred to a polyvinylidene difluoride (PVDF) membrane. After blocking with 5% milk, the COX-2/iNOS proteins were conjugated to a COX-2/iNOS specific antibodies, followed by a horseradish peroxidase conjugated second antibody. The proteins COX-2, iNOS, and β-actin (a constitutively expressed protein not affected by the treatments) were detected with Pierce Super Signal PICO West Chemiluminescent Substrate. Membranes were exposed to X-ray film and developed with darkroom methods. The protein bands were quantified using BioRad Quantity One software. The results showed that the cranberry polyphenols had the ability to inhibit iNOS expression relative to the positive LPS control.

TABLE 5

| Treatment | % LPS control |
|---|---|
| Negative control no LPS | 0 |
| Positive control LPS | 100 |
| LPS + 25 μg powder | 106 ± 13 |
| LPS + 50 μg powder | 108 ± 17 |
| LPS + 100 μg powder | 33 ± 6 |
| LPS + 200 μg powder | 4.0 ± 6 |

Example 7: Reduction of Oxidative Stress

The same materials, cranberry concentrate powder and Fraction E, were tested using an assay for generation of reactive oxygen species and their effect on HepG2 cells. Two different types of experiments were designed for this study: A) experiment of plain treatment of cells with cranberry concentrate powder and Fraction E for 24 hours to test for a direct effect of the tested extracts, and B) experiment of pre-treatment of cells with cranberry concentrate powder and Fraction E for 20 hours before submitting the cells to an oxidative stress by tertbutyl-hydroperoxide (t-BOOH) to test for a protective effect of the extracts against an oxidative insult. In the first experiment, cells were cultured in 24-well plates for 24 hours with the different concentrations cranberry concentrate powder and Fraction E, dissolved in distilled water, and then in serum-free culture medium, the dichorofluorescin (DCFH) probe was added for 30 minutes, then they were washed twice before being treated with plain serum-free medium and with (t-BOOH wells) or without (the rest of wells) 400 μM t-BOOH for 90 minutes. In the second experiment, the different concentrations of cranberry concentrate powder and Fraction E were added to the cell plates for 20 hours, the DCFH probe added for 30 minutes, then the cell plates were washed twice with PBS and new serum-free medium containing 400 μM t-BOOH was added to all cultures except controls for the 90 minutes of the assay.

Cellular oxidative stress was quantified by the dichlorofluorescein assay using microplate reader (Wang et al., Free Rad. Biol. Med. 1999, 27, 612-616; LeBel et al., Chem. Res. Toxicol. 1992, 5, 227-231). After adding conditions, multiwell plates were immediately measured (time=0) in a fluorescent microplate reader at excitation wavelength of 485 nm and emission wavelength of 530 nm. After being oxidized by intracellular oxidants, DCFH will become dichlorofluorescein (DCF) and emit fluorescence. By quantifying fluorescence, a fair estimation of the overall oxygen species generated under the different conditions was obtained (11-12).

Figure 4:
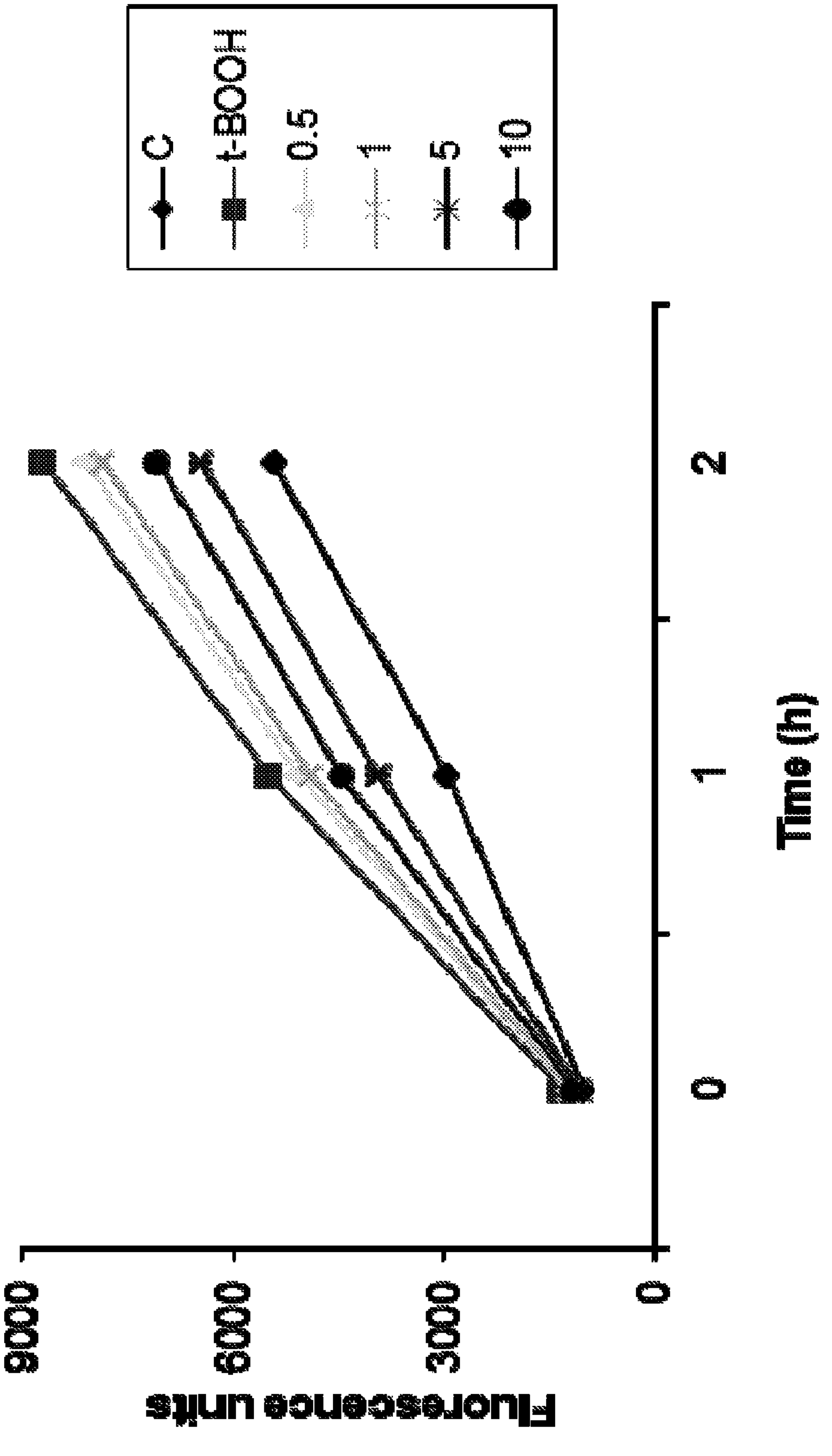
FIG. 4 is a line graph showing a dose response reduction in generation of reactive oxygen species in cells treated with cranberry Fraction E.

The results for cranberry concentrate powder and Fraction E showed that ROS generated by treatment with both at concentrations of 0.5-10 μg/ml compared to 400 μM t-BOOH for 90 minutes generated ROS levels that were clearly below those of control non-stressed cells. Pre-treatment of cells for 20 hours with Fraction E evoked a significant protection against t-BOOH-induced ROS overproduction. This protection followed a dose-response pattern, higher doses (5-10 μg/mL) showing a higher protection against the insult than the lower doses (0.5-1 μg/mL). These data suggest that high levels of ROS generated during the stress period are being more efficiently quenched in cells pre-treated with Fraction E resulting in reduced cell damage (FIG. 4).

Example 8: Clinical Trial

Subjects arrived for the initial blood draw (d=0) and were randomly assigned to the experimental treatment (cranberry beverage) and placebo groups. Both subjects and investigators were blinded as to the treatments. Ocean Spray, Inc. (Middleboro, Mass.) provided a cranberry beverage (CB) and the placebo beverage (PB), and recommended that unopened and opened bottles of beverage be stored refrigerated at 2-7° C. The cranberry beverage contained filtered water, cranberry components from concentrate, sugar, natural flavors, Red 40 and Blue 1 (colors), citric acid, and sucralose. The placebo beverage was a color, calorie, and sweetener-matched beverage without cranberry components. Every participant was given 72 bottles, each containing 450 mL (15 oz) of beverage, and was instructed to drink one bottle throughout the day, every day, for 70 days (10 weeks). Participants were instructed to return any remaining bottles at the end of the study.

Subjects were given a daily illness log to record any cold and flu symptoms during the 10 week experimental period. Primary outcomes were defined prospectively as incidence (number of illnesses, duration (number of days) and severity (total symptoms per total incidences). The symptoms assessed were: runny or congested nose, cough, sneezing, fever and/or chills, sore throat, headache, wheezing, and intestinal distress (which included nausea, vomiting, diarrhea, and/or abdominal cramps). Allergy symptoms were not included in the analysis. Subjects were also asked to report: if they missed class or work, if they sought medical treatment and were prescribed any medications as a result of seeking treatment, what over-the-counter medications they took, and if they had a significant decrease in activities due to illness symptoms (Table 6).

TABLE 6

| | Placebo | Cranberry Beverage |
|---|---|---|
| n = | 23 | 22 |
| Total Incidences reported | 26 (14) | 19 (15) |

TABLE 6-continued

| | Placebo | Cranberry Beverage |
|---|---|---|
| Total cold and flu symptoms | 292 | 213 |
| Total days missed work/school | 29 | 22 |
| Total times reported a decrease in activity | 25 | 17 |

At 10 weeks, study participants returned for a final blood draw and to complete an exit questionnaire. The exit questionnaire included questions to determine if subjects experienced any side effects from the beverage, took any vitamin/mineral or dietary supplements, or smoked cigarettes. To determine efficacy of blinding, subjects reported whether they thought they had received the research beverage or the placebo beverage, and why they thought that. Overall study compliance was assessed by participants self-reporting if they missed drinking the beverage during the study, and by counts of bottles of beverage returned at the end of the study.

In this experiment, the same protocol for the testing of the in vitro extracts was conducted but using PBMCs from subjects consuming a beverage made from Fraction E or placebo for 10 weeks. Blood was taken from the subjects and PBMCs were isolated. The PBMCs were treated as discussed in the in vitro section above. The results as shown in Table 7 showed that after 10 weeks supplementation, subjects consuming beverage containing Fraction E had 5-fold increase in gamma delta T cell proliferation. At the same time, it was shown that the increase in proliferation did not result in an increase in inflammatory markers such as IL-17 and TNF alpha.

TABLE 7

Proliferation of Gamma Delta T cells from Subjects Consuming Test Beverage Made from Fraction E Compared to Placebo

| γδ T Cell Proliferation | Placebo | Cranberry Beverage |
|---|---|---|
| | Ratio: 6 d culture to 0 d culture | |
| Baseline | $1.03 \pm 0.28^C$ | $0.94 \pm 0.28^C$ |
| 10 weeks | $2.23 \pm 0.27^B$ | $4.80 \pm 0.28^A$ |
| Treatment | $p < 0.001$ | |
| Time | $p < 0.001$ | |
| Interaction | $p < 0.001$ | |
| TNF-α | | |
| | pg/ml culture supernatant | |
| Baseline | 717.3 ± 94.7 | 881.9 ± 94.7 |
| 10 weeks | 610.7 ± 90.5 | 591.7 ± 90.1 |
| IL-17 Secretion by Cultured PBMC | | |
| | pg/ml culture supernatant | |
| Baseline | $147.2 \pm 9.3^B$ | $175.6 \pm 9.6^A$ |
| 10 weeks | $129.4 \pm 9.3^B$ | $142.6 \pm 9.6^B$ |
| Treatment | $p = 0.428$ | |
| Time | $p = 0.010$ | |
| Interaction | $p = 0.425$ | |

Figure 5:
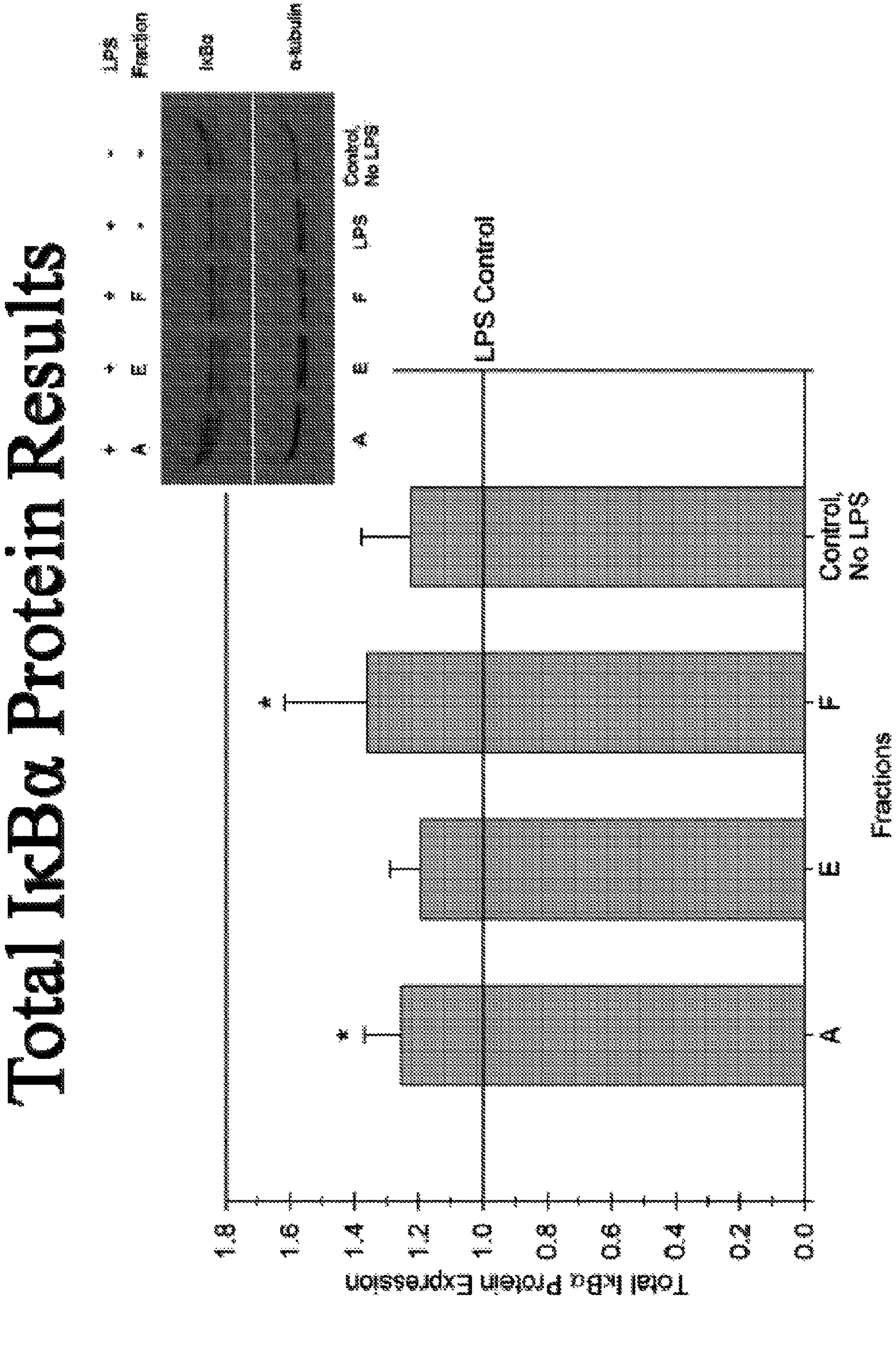
FIG. 5 is a bar graph and photomicrograph showing that total IKBα protein levels were higher lower in cells incubated with the CF compared to a LPS control.
Figure 6:
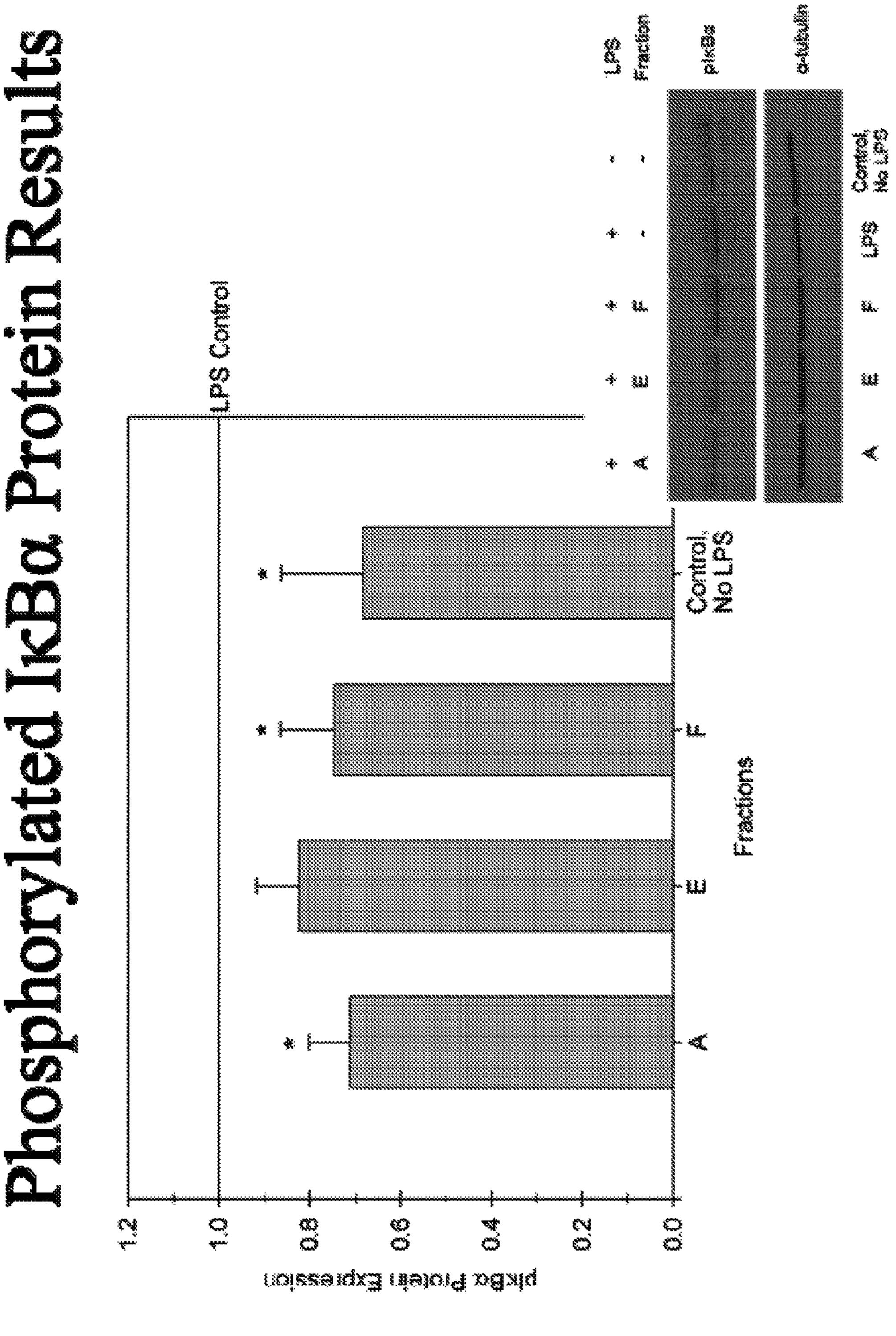
FIG. 6 is a bar graph and photomicrograph showing that phosphorylated IKBα protein levels were lower in cells incubated with the CF compared to a LPS control.
Figure 7:
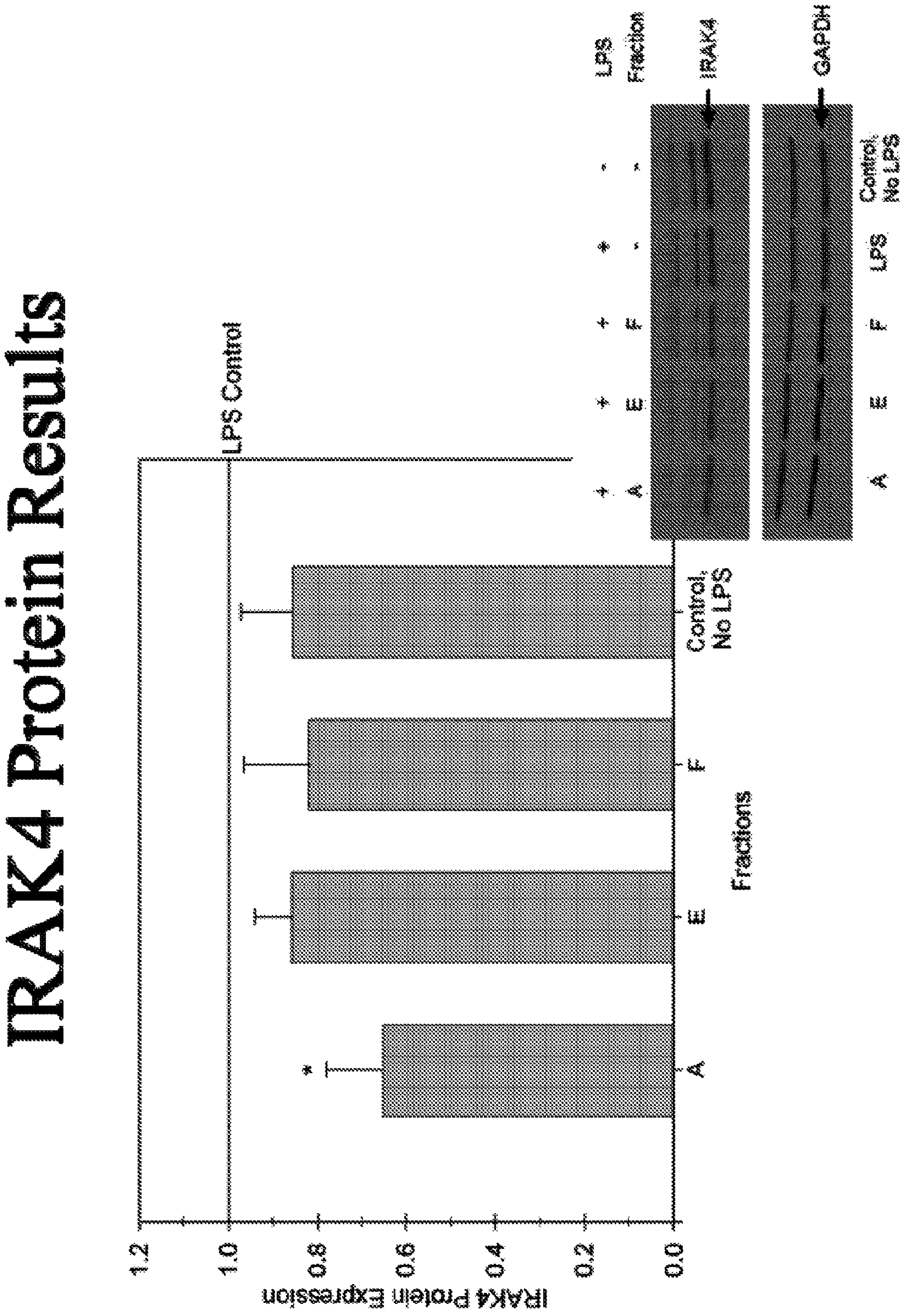
FIG. 7 is a bar graph and photomicrograph showing that IRAK4 protein levels were lower in cells incubated with the CF compared to a LPS control.
Figure 8:
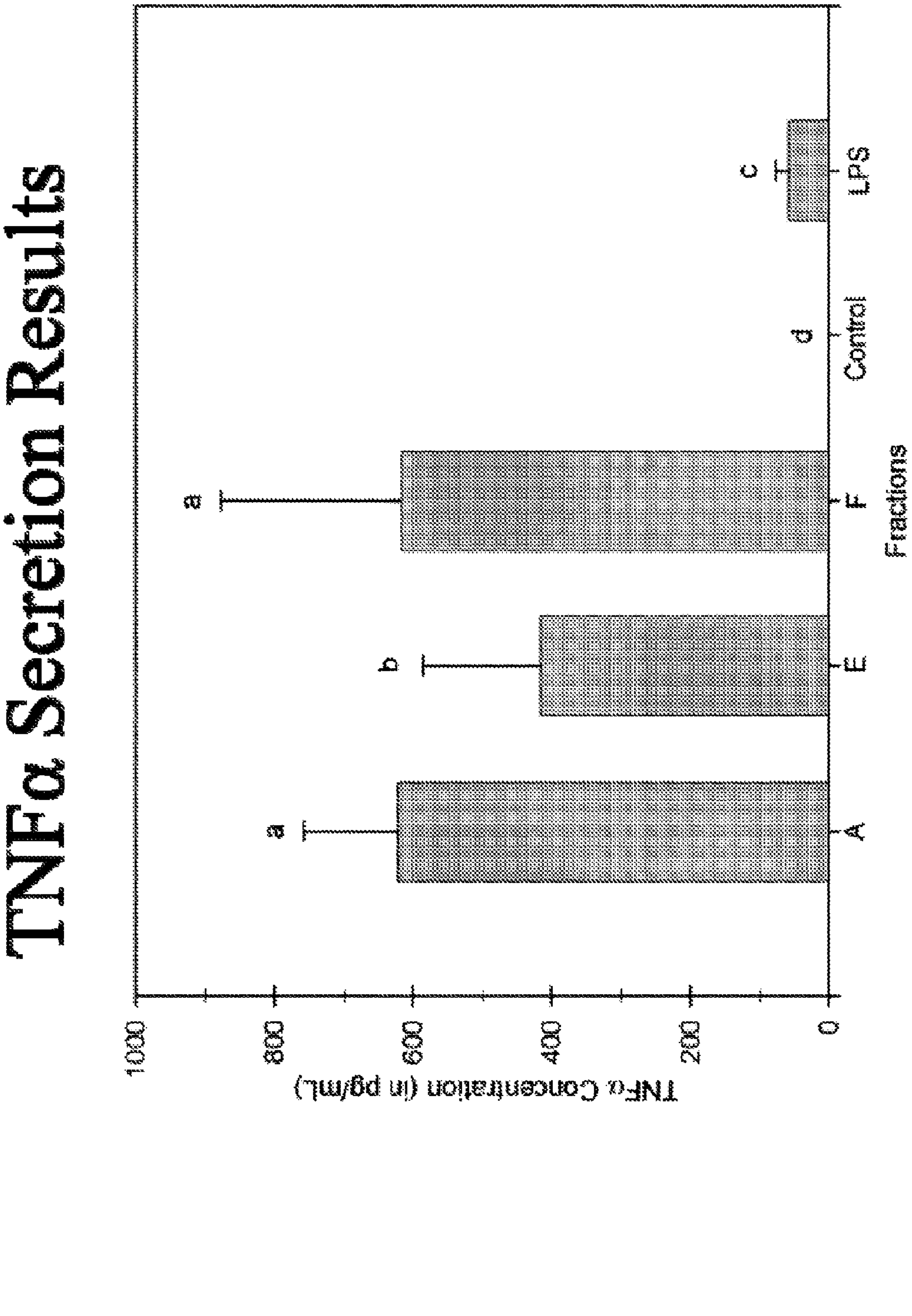
FIG. 8 is a bar graph showing TNFα secretion from cells incubated with CF was many fold higher than the LPS control.

Example 9: Cranberry Polyphenols Down-Regulate the Toll-Like Receptor 4 Pathway and NF-KB Activation, While Still Enhancing Tumor Necrosis Factor Secretion Polyphenols (PP) from plants have been shown to have anti-inflammatory properties. To study the anti-inflammatory nature of PP from cranberry, three cranberry fractions (CF) were incubated with HL60 cells, a human promyelocytic leukemia cell line. One CF contained PACs from cranberry presscake, one was rich in PAC from cranberry juice and the other contained PP, including PAC, from the juice. Differentiated HL60 cells were cultured with each CF and lipopolysaccharide (LPS). Phosphorylated IKBα and IRAK4 protein levels were lower in cells incubated with the CF compared to a LPS control, while total IKBα was increased by the CF compared to the LPS control (FIGS. 5-7). TNFα secretion from cells incubated with CF was higher than the LPS control (FIG. 8). Cranberry PP protects neutrophils from LPS activation via the Toll-like receptor 4 signaling pathway that uses IRAK4 as an intermediate signaling protein. IKBα is not phosphorylated and degraded, and, thus, does not release NF-KB. However, TNFα expression is still upregulated in fraction-treated cells, so its production and secretion is stimulated by these fractions via an alternate pathway.

Example 10: Effect of Cranberry Juice Intake on Human Gut Microbial Community and Urinary Metabolites in a Randomized, Placebo-Controlled Intervention Cranberry polyphenols support health by reducing pathogenic bacteria adhesion and growth. This randomized, double-blind, cross-over pilot study compared effects of consuming a light 27% cranberry juice beverage (LCB) vs. a placebo beverage (LPB) on fecal microbial community and urine metabolites. Healthy subjects (n=5), 20 to 40 years old, received 480 ml/d LPB or LCB in two 6-week intervention periods, with a 1 month washout. Fecal samples were collected at baseline, 3 and 6 weeks and 24 hour urine at baseline and 6 weeks. Microbial community structure, measured by terminal restriction fragment length polymorphism and quantitative PCR (QPCR) of the 16S rRNA gene, differed significantly (MRBP; p=0.036) between treatments at 6 weeks. Bifidobacteria (as % of total Eubacteria) significantly increased when subjects received the LCB (F=6.19, p<0.015) with no significant effect on *Bacterodetes, Lactobacillus* sp., *Enterobacteria*, or *C. coccoides/E. rectale* groups (by qPCR and adjusted for period effect). LCB intake significantly changed 49 urine metabolites, notably of nucleotide metabolism, and potential intake biomarkers, including protocatechuic acid-3-glucoside (Metabolon, Inc, NC) to help guide cranberry health research. The results suggest that cranberry juice intake may modulate human gut microbial community without decreasing percentages of some beneficial commensal bacteria.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing inflammatory disorder-associated gastrointestinal tract inflammation in a subject, the method comprising:

selecting a subject who has gastrointestinal tract inflammation associated with an inflammatory disorder selected from the group consisting of inflammatory bowel disease, Crohn's disease, ulcerative colitis, indeterminate colitis, microscopic colitis, collagenous colitis, and irritable bowel syndrome; and administering to the subject a composition comprising cranberry flavonols and cranberry proanthocyanidins in a ratio of about 1:4 to about 1:10 orally and in an amount effective to reduce gastrointestinal tract inflammation in the subject.

2. The method of claim 1, wherein the method further comprises administering an anti-inflammatory drug to the subject.

3. The method of claim 1, wherein the composition comprises at least about 50% proanthocyanidin by weight.

4. The method of claim 1, wherein the composition comprises at least about 1% flavonol by weight.

5. The method of claim 1, wherein the composition comprises about 70% proanthocyanidin by weight and about 10% flavonol by weight.

6. The method of claim 1, wherein an amount of the composition is administered to the subject such that the subject receives 20 to 500 mg of proanthocyanidin over 24 hours.

7. The method of claim 1, wherein the subject is a mammal.

8. The method claim 1, wherein the subject is a human.

9. The method of claim 1, wherein the inflammatory disorder is inflammatory bowel disease.

10. The method of claim 1, wherein the inflammatory disorder is Crohn's disease.

11. The method of claim 1, wherein the inflammatory disorder is ulcerative colitis.

12. The method of claim 1, wherein the inflammatory disorder is indeterminate colitis.

13. The method of claim 1, wherein the inflammatory disorder is microscopic colitis.

14. The method of claim 1, wherein the inflammatory disorder is collagenous colitis.

15. The method of claim 1, wherein the inflammatory disorder is irritable bowel syndrome.

16. The method of claim 1, wherein the composition has a ratio of flavonols to proanthocyanidins of about 1:4.

17. The method of claim 1, wherein the composition has a ratio of flavonols to proanthocyanidins of about 1:5.

18. The method of claim 1, wherein the composition has a ratio of flavonols to proanthocyanidins of about 1:6.

19. The method of claim 1, wherein the composition has a ratio of flavonols to proanthocyanidins of about 1:7.

20. The method of claim 1, wherein the composition has a ratio of flavonols to proanthocyanidins of about 1:8.

21. The method of claim 1, wherein the composition has a ratio of flavonols to proanthocyanidins of about 1:9.

22. The method of claim 1, wherein the composition has a ratio of flavonols to proanthocyanidins of about 1:10.

23. The method of claim 1, wherein the composition comprises about 70% proanthocyanidin by weight and about 7% flavonol by weight.

24. A method of reducing inflammatory disorder-associated gastrointestinal tract inflammation in a subject, the method comprising:

selecting a subject who has gastrointestinal tract inflammation associated with an inflammatory disorder selected from the group consisting of inflammatory bowel disease, Crohn's disease, ulcerative colitis, indeterminate colitis, microscopic colitis, collagenous colitis, and irritable bowel syndrome; and administering to the subject a composition consisting of cranberry flavonols and cranberry proanthocyanidins in a ratio of about 1:4 to about 1:10 orally and in an amount effective to reduce gastrointestinal tract inflammation in the subject.

25. The method of claim 24, wherein the composition comprises at least about 50% proanthocyanidin by weight.

26. The method of claim 24, wherein the composition comprises at least about 1% flavonol by weight.

27. The method of claim 24, wherein the composition comprises about 70% proanthocyanidin by weight and about 10% flavonol by weight.

28. The method of claim 24, wherein an amount of the composition is administered to the subject such that the subject receives 20 to 500 mg of proanthocyanidin over 24 hours.

29. The method of claim 24, wherein the subject is a mammal.

30. The method claim 24, wherein the subject is a human.

31. The method of claim 24, wherein the inflammatory disorder is inflammatory bowel disease.

32. The method of claim 24, wherein the inflammatory disorder is Crohn's disease.

33. The method of claim 24, wherein the inflammatory disorder is ulcerative colitis.

34. The method of claim 24, wherein the inflammatory disorder is indeterminate colitis.

35. The method of claim 24, wherein the inflammatory disorder is microscopic colitis.

36. The method of claim 24, wherein the inflammatory disorder is collagenous colitis.

37. The method of claim 24, wherein the inflammatory disorder is irritable bowel syndrome.

38. The method of claim 24, wherein the composition has a ratio of flavonols to proanthocyanidins of about 1:4.

39. The method of claim 24, wherein the composition has a ratio of flavonols to proanthocyanidins of about 1:5.

40. The method of claim 24, wherein the composition has a ratio of flavonols to proanthocyanidins of about 1:6.

41. The method of claim 24, wherein the composition has a ratio of flavonols to proanthocyanidins of about 1:7.

42. The method of claim 24, wherein the composition has a ratio of flavonols to proanthocyanidins of about 1:8.

43. The method of claim 24, wherein the composition has a ratio of flavonols to proanthocyanidins of about 1:9.

44. The method of claim 24, wherein the composition has a ratio of flavonols to proanthocyanidins of about 1:10.

45. The method of claim 24, wherein the composition comprises about 70% proanthocyanidin by weight and about 7% flavonol by weight.

* * * * *

UNITED STATES PATENT AND TRADEMARK OFFICE

CERTIFICATE OF CORRECTION

PATENT NO. : 9,895,341 B2
APPLICATION NO. : 14/008995
DATED : February 20, 2018
INVENTOR(S) : Christina Khoo et al.

It is certified that error appears in the above-identified patent and that said Letters Patent is hereby corrected as shown below:

In the Claims

In Column 20, Line 25, Claim 8, after "method" insert -- of --;

In Column 21, Line 17, Claim 30, after "method" insert -- of --.

Signed and Sealed this
Seventeenth Day of July, 2018

Andrei Iancu
*Director of the United States Patent and Trademark Office*